United States Patent [19]

Collins

[11] Patent Number: 5,917,025

[45] Date of Patent: Jun. 29, 1999

[54] HUMAN TELOMERASE

[75] Inventor: Kathleen Collins, Berkeley, Calif.

[73] Assignee: The Regents of the University of California, Oakland, Calif.

[21] Appl. No.: 09/098,487

[22] Filed: Jun. 16, 1998

Related U.S. Application Data

[62] Division of application No. 08/676,974, Jul. 8, 1996, Pat. No. 5,770,422.

[51] Int. Cl.⁶ .............................. C07H 21/04; C12N 9/12; C12N 1/20; C12N 15/00
[52] U.S. Cl. ...................... 536/23.2; 435/194; 435/252.3; 435/320.1; 435/91.31; 536/23.1; 536/24.31; 530/350
[58] Field of Search ................................... 435/91.3, 194, 435/240.1, 254.11, 252.3, 320.1, 91.1, 440, 442; 536/23.1, 23.2, 24.31, 24.33

[56] References Cited

U.S. PATENT DOCUMENTS 5,583,016  12/1996  Villeponteau et al. ................ 435/91.3

*Primary Examiner*—Robert A. Wax
*Assistant Examiner*—Tekchand Saidha
*Attorney, Agent, or Firm*—Richard Aron Osman

[57] ABSTRACT

The invention provides methods and compositions relating to a human telomerase and related nucleic acids, including four distinct human telomerase subunit proteins called p140, p105, p48 and p43 having human telomerase-specific activity. The proteins may be produced recombinantly from transformed host cells from the disclosed telomerase encoding nucleic acids or purified from human cells. Also included are human telomerase RNA components, as well as specific, functional derivatives thereof. The invention provides isolated telomerase hybridization probes and primers capable of specifically hybridizing with the disclosed telomerase gene, telomerase-specific binding agents such as specific antibodies, and methods of making and using the subject compositions in diagnosis, therapy and in the biopharmaceutical industry.

6 Claims, No Drawings

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 759 amino acids
      (B) TYPE: amino acid
      (C) STRANDEDNESS:
      (D) TOPOLOGY: Not Relevant (ii) MOLECULE TYPE: peptide (xi) SEQUENCE DESCRIPTION: SEQ ID NO:1:

```
Met Ala Gly Leu Thr Leu Phe Val Gly Arg Leu Pro Pro Ser Ala Arg
1               5                   10                  15

Ser Glu Gln Leu Glu Glu Leu Phe Ser Gln Val Gly Pro Val Lys Gln
                20                  25                  30

Cys Phe Val Val Thr Glu Lys Gly Ser Lys Ala Cys Arg Gly Phe Gly
            35                  40                  45

Tyr Val Thr Phe Ser Met Leu Glu Asp Val Gln Arg Ala Leu Lys Glu
        50                  55                  60

Ile Thr Thr Phe Glu Gly Cys Lys Ile Asn Val Thr Val Ala Lys Lys
65                  70                  75                  80

Lys Leu Arg Asn Lys Thr Lys Glu Lys Gly Lys Asn Glu Asn Ser Glu
                85                  90                  95

Cys Pro Lys Lys Glu Pro Lys Ala Lys Lys Ala Lys Val Ala Asp Lys
            100                 105                 110

Lys Ala Arg Leu Ile Ile Arg Asn Leu Ser Phe Lys Cys Ser Glu Asp
        115                 120                 125

Asp Leu Lys Thr Val Phe Ala Gln Phe Gly Ala Val Leu Glu Val Asn
130                 135                 140

Ile Pro Arg Lys Pro Asp Gly Lys Met Arg Gly Phe Gly Phe Val Gln
145                 150                 155                 160

Phe Lys Asn Leu Leu Glu Ala Gly Lys Ala Leu Lys Gly Met Asn Met
                165                 170                 175

Lys Glu Ile Lys Gly Arg Thr Val Ala Val Asp Trp Ala Val Ala Lys
            180                 185                 190

Asp Lys Tyr Lys Asp Thr Gln Ser Val Ser Ala Ile Gly Glu Glu Lys
        195                 200                 205

Ser His Glu Ser Lys His Gln Glu Ser Val Lys Lys Gly Arg Glu
210                 215                 220

Glu Glu Asp Met Glu Glu Glu Asn Asp Asp Asp Asp Asp
225                 230                 235                 240

Asp Glu Glu Asp Gly Val Phe Asp Asp Glu Glu Glu Asn
                245                 250                 255

Ile Glu Ser Lys Val Thr Lys Pro Val Gln Ile Gln Lys Arg Ala Val
            260                 265                 270

Lys Arg Pro Ala Pro Ala Lys Ser Ser Asp His Ser Glu Glu Asp Ser
        275                 280                 285

Asp Leu Glu Glu Ser Asp Ser Ile Asp Asp Gly Glu Glu Leu Ala Gln
290                 295                 300
```

-continued

```
Ser Asp Thr Ser Thr Glu Glu Gln Glu Asp Lys Ala Val Gln Val Ser
305                 310                 315                 320

Asn Lys Lys Lys Arg Lys Leu Pro Ser Asp Val Asn Glu Gly Lys Thr
            325                 330                 335

Val Phe Ile Arg Asn Leu Ser Phe Asp Ser Glu Glu Glu Leu Gly
                340                 345                 350

Glu Leu Leu Gln Gln Phe Gly Glu Leu Lys Tyr Val Arg Ile Val Leu
            355                 360                 365

His Pro Asp Thr Glu His Ser Lys Gly Cys Ala Phe Ala Gln Phe Met
        370                 375                 380

Thr Gln Glu Ala Ala Gln Lys Cys Leu Leu Ala Ala Ser Pro Glu Asn
385                 390                 395                 400

Glu Ala Gly Gly Leu Lys Leu Asp Gly Arg Gln Leu Lys Val Asp Leu
                405                 410                 415

Ala Val Thr Arg Asp Glu Ala Ala Lys Leu Gln Thr Thr Lys Val Lys
            420                 425                 430

Lys Pro Thr Gly Thr Arg Asn Leu Tyr Leu Ala Arg Glu Gly Leu Ile
            435                 440                 445

Arg Ala Gly Thr Lys Ala Ala Glu Gly Val Ser Ala Ala Asp Met Ala
        450                 455                 460

Lys Arg Glu Arg Phe Glu Leu Leu Lys His Gln Lys Leu Lys Asp Gln
465                 470                 475                 480

Asn Ile Phe Val Ser Arg Thr Arg Leu Cys Leu His Asn Leu Pro Lys
                485                 490                 495

Ala Val Asp Asp Lys Gln Leu Arg Lys Leu Leu Leu Ser Ala Thr Ser
            500                 505                 510

Gly Glu Lys Gly Val Arg Ile Lys Glu Cys Arg Val Met Arg Asp Leu
        515                 520                 525

Lys Gly Val His Gly Asn Met Lys Gly Gln Ser Leu Gly Tyr Ala Phe
530                 535                 540

Ala Glu Phe Gln Glu His Glu His Ala Leu Lys Ala Leu Arg Leu Ile
545                 550                 555                 560

Asn Asn Asn Pro Glu Ile Phe Gly Pro Leu Lys Arg Pro Ile Val Glu
                565                 570                 575

Phe Ser Leu Glu Asp Arg Arg Lys Leu Lys Met Lys Glu Leu Arg Ile
            580                 585                 590

Gln Arg Ser Leu Gln Lys Met Arg Ser Lys Pro Ala Thr Gly Glu Pro
        595                 600                 605

Gln Lys Gly Gln Pro Glu Pro Ala Lys Asp Gln Gln Gln Lys Ala Ala
610                 615                 620

Gln His His Thr Glu Glu Gln Ser Lys Val Pro Pro Glu Gln Lys Arg
625                 630                 635                 640

Lys Ala Gly Ser Thr Ser Trp Thr Gly Phe Gln Thr Lys Ala Glu Val
                645                 650                 655

Glu Gln Val Glu Leu Pro Asp Gly Lys Lys Arg Arg Lys Val Leu Ala
            660                 665                 670

Leu Pro Ser His Arg Gly Pro Lys Ile Arg Leu Arg Asp Lys Gly Lys
        675                 680                 685

Val Lys Pro Val His Pro Lys Pro Lys Pro Gln Ile Asn Gln Trp
690                 695                 700

Lys Gln Glu Lys Gln Gln Leu Ser Ser Glu Gln Val Ser Arg Lys Lys
705                 710                 715                 720

Ala Lys Gly Asn Lys Thr Glu Thr Arg Phe Asn Gln Leu Val Glu Gln
                725                 730                 735
```

```
            Tyr Lys Gln Lys Leu Leu Gly Pro Ser Lys Gly Ala Pro Leu Ala Lys
                            740                 745                 750

Arg Ser Lys Trp Phe Asp Ser
                    755

(2) INFORMATION FOR SEQ ID NO:2:

(i) SEQUENCE CHARACTERISTICS:
        (A) LENGTH: 2277 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:2:

ATGGCNGGNY TNACNYTNTT YGTNGGNMGN YTNCCNCCNW SNGCNMGNWS NGARCARYTN      60

GARGARYTNT TYWSNCARGT NGGNCCNGTN AARCARTGYT TYGTNGTNAC NGARAARGGN     120

WSNAARGCNT GYMGNGGNTT YGGNTAYGTN ACNTTYWSNA TGYTNGARGA YGTNCARMGN     180

GCNYTNAARG ARATHACNAC NTTYGARGGN TGYAARATHA AYGTNACNGT NGCNAARAAR     240

AARYTNMGNA AYAARACNAA RGARAARGGN AARAAYGARA AYWSNGARTG YCCNAARAAR     300

GARCCNAARG CNAARAARGC NAARGTNGCN GAYAARAARG CNMGNYTNAT HATHMGNAAY     360

YTNWSNTTYA ARTGYWSNGA RGAYGAYYTN AARACNGTNT TYGCNCARTT YGGNGCNGTN     420

YTNGARGTNA AYATHCCNMG NAARCCNGAY GGNAARATGM GNGGNTTYGG NTTYGTNCAR     480

TTYAARAAYY TNYTNGARGC NGGNAARGCN YTNAARGGNA TGAAYATGAA RGARATHAAR     540

GGNMGNACNG TNGCNGTNGA YTGGGCNGTN GCNAARGAYA ARTAYAARGA YACNCARWSN     600

GTNWSNGCNA THGGNGARGA RAARWSNCAY GARWSNAARC AYCARGARWS NGTNAARAAR     660

AARGGNMGNG ARGARGARGA YATGGARGAR GARGARAAYG AYGAYGAYGA YGAYGAYGAY     720

GAYGARGARG AYGGNGTNTT YGAYGAYGAR GAYGARGARG ARGARAAYAT HGARWSNAAR     780

GTNACNAARC CNGTNCARAT HCARAARMGN GCNGTNAARM GNCCNGCNCC NGCNAARWSN     840

WSNGAYCAYW SNGARGARGA YWSNGAYYTN GARGARWSNG AYWSNATHGA YGAYGGNGAR     900

GARYTNGCNC ARWSNGAYAC NWSNACNGAR GARCARGARG AYAARGCNGT NCARGTNWSN     960

AAYAARAARA ARMGNAARYT NCCNWSNGAY GTNAAYGARG GNAARACNGT NTTYATHMGN    1020

AAYYTNWSNT TYGAYWSNGA RGARGARGAR YTNGGNGARY TNYTNCARCA RTTYGGNGAR    1080

YTNAARTAYG TNMGNATHGT NYTNCAYCCN GAYACNGARC AYWSNAARGG NTGYGCNTTY    1140

GCNCARTTYA TGACNCARGA RGCNGCNCAR AARTGYYTNY TNGCNGCNWS NCCNGARAAY    1200

GARGCNGGNG GNYTNAARYT NGAYGGNMGN CARYTNAARG TNGAYYTNGC NGTNACNMGN    1260

GAYGARGCNG CNAARYTNCA RACNACNAAR GTNAARAARC CNACNGGNAC NMGNAAYYTN    1320

TAYYTNGCNM GNARGGNYT NATHMGNGCN GGNACNAARG CNGCNGARGG NGTNWSNGCN    1380

GCNGAYATGG CNAARMGNGA RMGNTTYGAR YTNYTNAARC AYCARAARYT NAARGAYCAR    1440

AAYATHTTYG TNWSNMGNAC NMGNYTNTGY YTNCAYAAYY TNCCNAARGC NGTNGAYGAY    1500

AARCARYTNM GNAARYTNYT NYTNWSNGCN ACNWSNGGNG ARAARGGNGT NMGNATHAAR    1560

GARTGYMGNG TNATGMGNGA YYTNAARGGN GTNCAYGGNA AYATGAARGG NCARWSNYTN    1620

GGNTAYGCNT TYGCNGARTT YCARGARCAY GARCAYGCNY TNAARGCNYT NMGNYTNATH    1680

AAYAAYAAYC CNGARATHTT YGGNCCNYTN AARMGNCCNA THGTNGARTT YWSNYTNGAR    1740

GAYMGNMGNA ARYTNAARAT GAARGARYTN MGNATHCARM GNWSNYTNCA RAARATGMGN    1800
```

-continued

```
WSNAARCCNG CNACNGGNGA RCCNCARAAR GGNCARCCNG ARCCNGCNAA RGAYCARCAR      1860

CARAARGCNG CNCARCAYCA YACNGARGAR CARWSNAARG TNCCNCCNGA RCARAARMGN      1920

AARGCNGGNW SNACNWSNTG GACNGGNTTY CARACNAARG CNGARGTNGA RCARGTNGAR      1980

YTNCCNGAYG GNAARAARMG NMGNAARGTN YTNGCNYTNC CNWSNCAYMG NGGNCCNAAR      2040

ATHMGNYTNM GNGAYAARGG NAARGTNAAR CCNGTNCAYC CNAARAARCC NAARCCNCAR      2100

ATHAAYCART GGAARCARGA RAARCARCAR YTNWSNWSNG ARCARGTNWS NMGNAARAAR      2160

GCNAARGGNA AYAARACNGA RACNMGNTTY AAYCARYTNG TNGARCARTA YAARCARAAR      2220

YTNYTNGGNC CNWSNAARGG NGCNCCNYTN GCNAARMGNW SNAARTGGTT YGAYWSN        2277
```

(2) INFORMATION FOR SEQ ID NO:3:

(i) SEQUENCE CHARACTERISTICS:
        (A) LENGTH: 2733 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:3:

```
TGAGCTTGGT TGTCCTACCA AAGCCAGCGT TTCGGCTCGC GTGCGCCGGC CTAGTTTGCT        60

CGCGTCCTCA CGCGCTTTGG GTTTCCCGGT CTCATGGCCG GCCTGACCTT ATTTGTGGGC       120

CGCCTCCCGC CCTCGGCCCG CAGTGAGCAG CTGGAGGAAC TGTTCAGTCA GGTGGGGCCG       180

GTGAAGCAGT GCTTCGTGGT GACTGAAAAA GGGAGTAAGG CATGTCGAGG CTTTGGCTAT       240

GTCACTTTTT CAATGCTGGA AGATGTTCAG AGGGCCCTCA AGGAGATTAC CACCTTTGAA       300

GGTTGCAAGA TCAACGTGAC TGTTGCCAAG AAAAAACTGA GGAACAAGAC AAAGGAAAAG       360

GGGAAAAATG AAAACTCAGA GTGCCCAAAG AAGGAGCCGA AGGCTAAAAA AGCCAAAGTG       420

GCAGATAAGA AAGCCAGATT AATTATTCGG AACCTGAGCT TTAAGTGTTC AGAAGATGAC       480

TTGAAGACAG TATTTGCTCA ATTTGGAGCT GTCCTGGAAG TAAATATCCC TAGGAAACCA       540

GATGGGAAGA TGCGCGGTTT TGGTTTTGTT CAGTTCAAAA ACCTCCTAGA AGCAGGTAAA       600

GCTCTCAAAG GCATGAACAT GAAAGAGATA AAAGGCCGGA CAGTGGCTGT GGATTGGGCC       660

GTGGCAAAGG ATAAATATAA AGATACACAG TCTGTTTCTG CTATAGGTGA GGAAAAGAGC       720

CATGAATCTA AACATCAGGA ATCAGTTAAA AAGAAGGGCA GAGAGGAAGA GGATATGGAA       780

GAGGAAGAAA ACGATGATGA TGACGATGAT GATGATGAAG AAGATGGGGT TTTTGATGAT       840

GAAGATGAAG AGGAAGAGAA TATAGAATCA AAGGTGACCA AGCCTGTGCA AATTCAGAAG       900

AGAGCAGTCA AGAGACCAGC CCCTGCAAAA AGCAGTGATC ATTCTGAGGA GGACAGTGAC       960

CTAGAGGAAA GCGATAGTAT TGATGATGGA GAGGAACTGG CTCAGAGTGA TACCAGCACT      1020

GAGGAGCAAG AGGATAAAGC TGTGCAAGTC TCAAACAAAA AGAAGAGGAA ATTACCCTCT      1080

GATGTGAATG AAGGGAAAAC TGTTTTTATC AGAAATCTGT CCTTTGACTC AGAAGAAGAA      1140

GAACTTGGGG AGCTTCTCCA ACAGTTTGGA GAACTCAAAT ATGTCCGCAT TGTCTTGCAT      1200

CCAGACACAG AGCATTCTAA AGGTTGTGCA TTTGCCCAGT TCATGACTCA AGAAGCAGCT      1260

CAGAAATGCC TTCTAGCTGC TTCTCCAGAG AATGAGGCTG GTGGGCTTAA ACTGGATGGC      1320

CGGCAGCTCA AGGTTGACTT GGCGGTGACC CGTGATGAGG CTGCAAAGCT TCAGACGACG      1380

AAGGTGAAGA AGCCGACTGG CACCCGGAAT CTCTATCTGG CCCGAGAAGG CTTGATTCGT      1440

GCTGGGACGA AGGCTGCAGA GGGTGTGAGT GCTGCTGATA TGGCCAAAAG AGAACGGTTT      1500

GAGCTGCTGA AGCATCAGAA ACTCAAGGAC CAGAATATCT TTGTCTCCCG AACCAGGCTC      1560
```

```
TGCCTGCACA ATCTCCCAAA GGCTGTAGAT GACAAACAGC TCAGAAAGCT GCTGCTGAGT      1620

GCTACTAGTG GAGAGAAAGG GGTGCGCATC AAGGAGTGTA GAGTGATGCG AGACCTCAAA      1680

GGAGTTCATG GGAACATGAA GGGTCAGTCC CTGGGCTACG CCTTTGCGGA GTTCCAAGAG      1740

CACGAGCATG CCCTGAAAGC CCTCCGCCTC ATCAACAACA ATCCAGAAAT CTTTGGGCCT      1800

CTGAAGAGAC CAATAGTGGA GTTCTCTTTA GAAGATCGAA GAAAACTTAA AATGAAGGAA      1860

TTAAGGATCC AGCGCAGCTT GCAAAAAATG AGATCCAAGC CTGCAACTGG TGAGCCTCAG      1920

AAGGGGCAAC CAGAGCCTGC AAAAGACCAG CAACAGAAGG CAGCTCAACA CCACACAGAG      1980

GAACAAAGCA AGGTGCCCCC AGAGCAGAAG AGAAAGGCGG GCTCTACCTC ATGGACCGGG      2040

TTCCAGACCA AGGCTGAAGT GGAGCAGGTG GAGCTGCCTG ATGGAAAGAA GAGAAGAAAG      2100

GTCCTGGCGC TCCCCTCACA CCGAGGCCCC AAAATCAGGT TGCGGGACAA AGGCAAAGTG      2160

AAGCCCGTCC ATCCCAAAAA GCCAAAGCCA CAGATAAACC AGTGGAAGCA GGAGAAGCAG      2220

CAATTATCGT CCGAGCAGGT ATCTAGGAAA AAAGCTAAGG GAAATAAGAC GGAAACCCGC      2280

TTCAACCAGC TGGTCGAACA ATATAAGCAG AAATTATTGG GACCTTCTAA AGGAGCACCT      2340

CTTGCAAAGA GGAGCAAATG GTTTGATAGT TGATGATGGC AGCAGGCTGG GTAAGAAGCT      2400

GGGTTGTATA CTTTCTGGTG ACACTCCTGG GCTCCTCCCC ATCCCCGTG TCTCTCACTG       2460

AGGGAAAGAA AATCCCCAAG GGCACTGCCA CTGTGCTCGG AGGTGCCCTG GACTGTGTAC      2520

ATCTGAACTT TGGTCCATCC TTTGATGTGT GGTTCGTTAG CCACAAAGAG AAATATCTGA     2580

AAGTCAACAT GATGCTTCTT GCATATTATC CAGATTATTG TATGAAGTTG TGTCTATAAT      2640

TATTACCAAT TTTTATTCTT TATTTCTCAA ATGGAAACAC CTGAAAAAGC AAAAAAAAAA      2700

AAAAAAAAAA CTCGAGGGGG GCCCGTACCC AAT                                  2733

(2) INFORMATION FOR SEQ ID NO:4:

(i) SEQUENCE CHARACTERISTICS:
            (A) LENGTH: 2277 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:4:

AUGGCUGGUC UGACCCUGUU CGUUGGUCGU CUGCCGCCGU CCGCUCGUUC CGAACAGCUG        60

GAAGAACUGU UCUCCCAGGU UGGUCCGGUU AAACAGUGCU UCGUUGUUAC CGAAAAAGGU       120

UCCAAAGCUU GCCGUGGUUU CGGUUACGUU ACCUUCUCCA UGCUGGAAGA CGUUCAGCGU       180

GCUCUGAAAG AAAUCACCAC CUUCGAAGGU UGCAAAAUCA ACGUUACCGU UGCUAAAAAA       240

AAACUGCGUA ACAAAACCAA AGAAAAAGGU AAAAACGAAA ACUCCGAAUG CCCGAAAAAA       300

GAACCGAAAG CUAAAAAAGC UAAAGUUGCU GACAAAAAAG CUCGUCUGAU CAUCCGUAAC       360

CUGUCCUUCA AAUGCUCCGA AGACGACCUG AAAACCGUUU UCGCUCAGUU CGGUGCUGUU       420

CUGGAAGUUA ACAUCCCGCG UAAACGGGAC GGUAAAAUGC GUGGUUUCGG UUUCGUUCAG       480

UUCAAAAACC UGCUGGAAGC UGGUAAAGCU CUGAAAGGUA UGAACAUGAA AGAAAUCAAA       540

GGUCGUACCG UUGCUGUUGA CUGGGCUGUU GCUAAAGACA AAUACAAAGA CACCCAGUCC       600

GUUUCCGCUA UCGGUGAAGA AAAAUCCCAC GAAUCCAAAC ACCAGGAAUC CGUUAAAAAA       660

AAAGGUCGUG AAGAAGAAGA CAUGGAAGAA GAAGAAAACG ACGACGACGA CGACGACGAC       720

GACGAAGAAG ACGGUGUUUU CGACGACGAA GACGAAGAAG AAGAAAACAU CGAAUCCAAA       780
```

```
GUUACCAAAC CGGUUCAGAU CCAGAAACGU GCUGUUAAAC GUCCGGCUCC GGCUAAAUCC      840

UCCGACCACU CCGAAGAAGA CUCCGACCUG GAAGAAUCCG ACUCCAUCGA CGACGGUGAA      900

GAACUGGCUC AGUCCGACAC CUCCACCGAA GAACAGGAAG ACAAAGCUGU UCAGGUUUCC      960

AACAAAAAAA AACGUAAACU GCCGUCCGAC GUUAACGAAG GUAAAACCGU UUUCAUCCGU     1020

AACCUGUCCU UCGACUCCGA AGAAGAAGAA CUGGGUGAAC UGCUGCAGCA GUUCGGUGAA     1080

CUGAAAUACG UUCGUAUCGU UCUGCACCCG GACACCGAAC ACUCCAAAGG UUGCGCUUUC     1140

GCUCAGUUCA UGACCCAGGA AGCUGCUCAG AAAUGCCUGC UGGCUGCUUC CCCGGAAAAC     1200

GAAGCUGGUG GUCUGAAACU GGACGGUCGU CAGCUGAAAG UUGACCUGGC UGUUACCCGU     1260

GACGAAGCUG CUAAACUGCA GACCACCAAA GUUAAAAAAC CGACCGGUAC CCGUAACCUG     1320

UACCUGGCUC GUGAAGGUCU GAUCCGUGCU GGUACCAAAG CUGCUGAAGG UGUUUCCGCU     1380

GCUGACAUGG CUAAACGUGA ACGUUUCGAA CUGCUGAAAC ACCAGAAACU GAAAGACCAG     1440

AACAUCUUCG UUUCCCGUAC CGUCUGUGC CUGCACAACC UGCCGAAAGC UGUUGACGAC     1500

AAACAGCUGC GUAAACUGCU GCUGUCCGCU ACCUCCGGUG AAAAAGGUGU UCGUAUCAAA     1560

GAAUGCCGUG UUAUGCGUGA CCUGAAAGGU GUUCACGGUA ACAUGAAAGG UCAGUCCCUG     1620

GGUUACGCUU UCGCUGAAUU CCAGGAACAC GAACACGCUC UGAAAGCUCU GCGUCUGAUC     1680

AACAACAACC CGGAAAUCUU CGGUCCGCUG AAACGUCCGA UCGUUGAAUU CUCCCUGGAA     1740

GACCGUCGUA AACUGAAAAU GAAAGAACUG CGUAUCCAGC GUUCCCUGCA GAAAAUGCGU     1800

UCCAAACCGG CUACCGGUGA ACCGCAGAAA GGUCAGCCGG AACCGGCUAA AGACCAGCAG     1860

CAGAAAGCUG CUCAGCACCA CACCGAAGAA CAGUCCAAAG UUCCGCCGGA ACAGAAACGU     1920

AAAGCUGGUU CCACCUCCUG GACCGGUUUC CAGACCAAAG CUGAAGUUGA ACAGGUUGAA     1980

CUGCCGGACG GUAAAAAACG UCGUAAAGUU CUGGCUCUGC CGUCCCACCG UGGUCCGAAA     2040

AUCCGUCUGC GUGACAAAGG UAAAGUUAAA CCGGUUCACC CGAAAAAACC GAAACCGCAG     2100

AUCAACCAGU GGAAACAGGA AAAACAGCAG CUGUCCUCCG AACAGGUUUC CGUAAAAAA     2160

GCUAAAGGUA ACAAAACCGA AACCCGUUUC AACCAGCUGG UUGAACAGUA CAAACAGAAA     2220

CUGCUGGGUC CGUCCAAAGG UGCUCCGCUG GCUAAACGUU CCAAAUGGUU CGACUCC      2277

(2) INFORMATION FOR SEQ ID NO:5:

(i) SEQUENCE CHARACTERISTICS:
        (A) LENGTH: 2277 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:5:

ATGGCCGGCC TGACCCTGTT CGTGGGCCGC CTGCCCCCCA GCGCCCGCAG CGAGCAGCTG       60

GAGGAGCTGT TCAGCCAGGT GGGCCCCGTG AAGCAGTGCT TCGTGGTGAC CGAGAAGGGC      120

AGCAAGGCCT GCCGCGGCTT CGGCTACGTG ACCTTCAGCA TGCTGGAGGA CGTGCAGCGC      180

GCCCTGAAGG AGATCACCAC CTTCGAGGGC TGCAAGATCA ACGTGACCGT GGCCAAGAAG      240

AAGCTGCGCA ACAAGACCAA GGAGAAGGGC AAGAACGAGA CAGCGAGTG CCCCAAGAAG       300

GAGCCCAAGG CCAAGAAGGC CAAGGTGGCC GACAAGAAGG CCCGCCTGAT CATCCGCAAC      360

CTGAGCTTCA AGTGCAGCGA GGACGACCTG AAGACCGTGT TCGCCCAGTT CGGCGCCGTG      420

CTGGAGGTGA ACATCCCCCG CAAGCCCGAC GGCAAGATGC GCGGCTTCGG CTTCGTGCAG      480

TTCAAGAACC TGCTGGAGGC CGGCAAGGCC CTGAAGGGCA TGAACATGAA GGAGATCAAG      540
```

```
GGCCGCACCG TGGCCGTGGA CTGGGCCGTG GCCAAGGACA AGTACAAGGA CACCCAGAGC      600

GTGAGCGCCA TCGGCGAGGA GAAGAGCCAC GAGAGCAAGC ACCAGGAGAG CGTGAAGAAG      660

AAGGGCCGCG AGGAGGAGGA CATGGAGGAG GAGGAGAACG ACGACGACGA CGACGACGAC      720

GACGAGGAGG ACGGCGTGTT CGACGACGAG GACGAGGAGG AGGAGAACAT CGAGAGCAAG      780

GTGACCAAGC CCGTGCAGAT CCAGAAGCGC GCCGTGAAGC GCCCCGCCCC CGCCAAGAGC      840

AGCGACCACA GCGAGGAGGA CAGCGACCTG GAGGAGAGCG ACAGCATCGA CGACGGCGAG      900

GAGCTGGCCC AGAGCGACAC CAGCACCGAG GAGCAGGAGG ACAAGGCCGT GCAGGTGAGC      960

AACAAGAAGA AGCGCAAGCT GCCCAGCGAC GTGAACGAGG GCAAGACCGT GTTCATCCGC     1020

AACCTGAGCT TCGACAGCGA GGAGGAGGAG CTGGGCGAGC TGCTGCAGCA GTTCGGCGAG     1080

CTGAAGTACG TGCGCATCGT GCTGCACCCC GACACCGAGC ACAGCAAGGG CTGCGCCTTC     1140

GCCCAGTTCA TGACCCAGGA GGCCGCCCAG AAGTGCCTGC TGGCCGCCAG CCCCGAGAAC     1200

GAGGCCGGCG GCCTGAAGCT GGACGGCCGC CAGCTGAAGG TGGACCTGGC CGTGACCCGC     1260

GACGAGGCCG CCAAGCTGCA GACCACCAAG GTGAAGAAGC CCACCGGCAC CCGCAACCTG     1320

TACCTGGCCC GCGAGGGCCT GATCCGCGCC GGCACCAAGG CCGCCGAGGG CGTGAGCGCC     1380

GCCGACATGG CCAAGCGCGA GCGCTTCGAG CTGCTGAAGC ACCAGAAGCT GAAGGACCAG     1440

AACATCTTCG TGAGCCGCAC CCGCCTGTGC CTGCACAACC TGCCCAAGGC CGTGGACGAC     1500

AAGCAGCTGC GCAAGCTGCT GCTGAGCGCC ACCAGCGGCG AGAAGGGCGT GCGCATCAAG     1560

GAGTGCCGCG TGATGCGCGA CCTGAAGGGC GTGCACGGCA ACATGAAGGG CCAGAGCCTG     1620

GGCTACGCCT TCGCCGAGTT CCAGGAGCAC GAGCACGCCC TGAAGGCCCT GCGCCTGATC     1680

AACAACAACC CCGAGATCTT CGGCCCCCTG AAGCGCCCCA TCGTGGAGTT CAGCCTGGAG     1740

GACCGCCGCA AGCTGAAGAT GAAGGAGCTG CGCATCCAGC GCAGCCTGCA GAAGATGCGC     1800

AGCAAGCCCG CCACCGGCGA GCCCCAGAAG GGCCAGCCCG AGCCCGCCAA GGACCAGCAG     1860

CAGAAGGCCG CCCAGCACCA CACCGAGGAG CAGAGCAAGG TGCCCCCCGA GCAGAAGCGC     1920

AAGGCCGGCA GCACCAGCTG GACCGGCTTC CAGACCAAGG CCGAGGTGGA GCAGGTGGAG     1980

CTGCCCGACG GCAAGAAGCG CCGCAAGGTG CTGGCCCTGC CCAGCCACCG CGGCCCCAAG     2040

ATCCGCCTGC GCGACAAGGG CAAGGTGAAG CCCGTGCACC CCAAGAAGCC CAAGCCCCAG     2100

ATCAACCAGT GGAAGCAGGA GAAGCAGCAG CTGAGCAGCG AGCAGGTGAG CCGCAAGAAG     2160

GCCAAGGGCA ACAAGACCGA GACCCGCTTC AACCAGCTGG TGGAGCAGTA CAAGCAGAAG     2220

CTGCTGGGCC CCAGCAAGGG CGCCCCCCTG GCCAAGCGCA GCAAGTGGTT CGACAGC        2277

(2) INFORMATION FOR SEQ ID NO:6:

(i) SEQUENCE CHARACTERISTICS:
        (A) LENGTH: 540 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:6:

GGGTTGCGGA GGGTGGGCCT GGGAGGGGTG GTGGCCATTT TTTGTCTAAC CCTAACTGAG       60

AAGGGCGTAG GCGCCGTGCT TTTGCTCCCC GCGCGCTGTT TTTCTCGCTG ACTTTCAGCG      120

GGCGGAAAAG CCTCGGCCTG CCGCCTTCCA CCGTTCATTC TAGAGCAAAC AAAAAATGTC      180

AGCTGCTGGC CCGTTCGCCC CTCCCGGGGA CCTGCGGCGG GTCGCCTGCC CAGCCCCCGA      240
```

```
ACCCCGCCTG GAGGCCGCGG TCGGCCCGGG GCTTCTCCGG AGGCACCCAC TGCCACCGCG    300

AAGAGTTGGG CTCTGTCAGC CGCGGGTCTC TCGGGGCGA GGGCGAGGTT CAGGCCTTTC     360

AGGCCGCAGG AAGAGGAACG GAGCGAGTCC CCGCGCGCGG CGCGATTCCC TGAGCTGTGG    420

GACGTGCACC CAGGACTCGG CTCACACATG CAGTTCGCTT TCCTGTTGGT GGGGGGAACG    480

CCGATCGTGC GCATCCGTCA CCCCTCGCCG GCAGTGGGGG CTTGTGAACC CCCAAACCTG    540

(2) INFORMATION FOR SEQ ID NO:7:

(i) SEQUENCE CHARACTERISTICS:
        (A) LENGTH: 540 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:7:

GGGTTGCGGA GGGTGGGCCT GGGAGGGGTG GTGGCCATTT TTTGTCCAAC CCCAACTGAG     60

AAGGGCGTAG GCGCCGTGCT TTTGCTCCCC GCGCGCTGTT TTTCTCGCTG ACTTTCAGCG    120

GGCGGAAAAG CCTCGGCCTG CCGCCTTCCA CCGTTCATTC TAGAGCAAAC AAAAAATGTC    180

AGCTGCTGGC CCGTTCGCCC CTCCCGGGGA CCTGCGGCGG GTCGCCTGCC CAGCCCCCGA    240

ACCCCGCCTG GAGGCCGCGG TCGGCCCGGG GCTTCTCCGG AGGCACCCAC TGCCACCGCG    300

AAGAGTTGGG CTCTGTCAGC CGCGGGTCTC TCGGGGCGA GGGCGAGGTT CAGGCCTTTC     360

AGGCCGCAGG AAGAGGAACG GAGCGAGTCC CCGCGCGCGG CGCGATTCCC TGAGCTGTGG    420

GACGTGCACC CAGGACTCGG CTCACACATG CAGTTCGCTT TCCTGTTGGT GGGGGGAACG    480

CCGATCGTGC GCATCCGTCA CCCCTCGCCG GCAGTGGGGG CTTGTGAACC CCCAAACCTG    540

(2) INFORMATION FOR SEQ ID NO:8:

(i) SEQUENCE CHARACTERISTICS:
        (A) LENGTH: 540 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:8:

GGGTTGCGGA GGGTGGGCCT GGGAGGGGTG GTGGCCATTT TTTGTCTAAG CCTAAGTGAG     60

AAGGGCGTAG GCGCCGTGCT TTTGCTCCCC GCGCGCTGTT TTTCTCGCTG ACTTTCAGCG    120

GGCGGAAAAG CCTCGGCCTG CCGCCTTCCA CCGTTCATTC TAGAGCAAAC AAAAAATGTC    180

AGCTGCTGGC CCGTTCGCCC CTCCCGGGGA CCTGCGGCGG GTCGCCTGCC CAGCCCCCGA    240

ACCCCGCCTG GAGGCCGCGG TCGGCCCGGG GCTTCTCCGG AGGCACCCAC TGCCACCGCG    300

AAGAGTTGGG CTCTGTCAGC CGCGGGTCTC TCGGGGCGA GGGCGAGGTT CAGGCCTTTC     360

AGGCCGCAGG AAGAGGAACG GAGCGAGTCC CCGCGCGCGG CGCGATTCCC TGAGCTGTGG    420

GACGTGCACC CAGGACTCGG CTCACACATG CAGTTCGCTT TCCTGTTGGT GGGGGGAACG    480

CCGATCGTGC GCATCCGTCA CCCCTCGCCG GCAGTGGGGG CTTGTGAACC CCCAAACCTG    540

(2) INFORMATION FOR SEQ ID NO:9:

(i) SEQUENCE CHARACTERISTICS:
        (A) LENGTH: 538 base pairs
        (B) TYPE: nucleic acid
```

(C) STRANDEDNESS: double
        (D) TOPOLOGY: linear (ii) MOLECULE TYPE: cDNA (xi) SEQUENCE DESCRIPTION: SEQ ID NO:9:

```
GGGTTGCGGA GGGTGGGCCT GGGAGGGGTG GTGGCCATTT TTTGTCTACC CTACTGAGAA      60
GGGCGTAGGC GCCGTGCTTT TGCTCCCCGC GCGCTGTTTT TCTCGCTGAC TTTCAGCGGG     120
CGGAAAAGCC TCGGCCTGCC GCCTTCCACC GTTCATTCTA GAGCAAACAA AAAATGTCAG     180
CTGCTGGCCC GTTCGCCCCT CCCGGGGACC TGCGGCGGGT CGCCTGCCCA GCCCCCGAAC     240
CCCGCCTGGA GGCCGCGGTC GGCCCGGGGC TTCTCCGGAG GCACCCACTG CCACCGCGAA     300
GAGTTGGGCT CTGTCAGCCG CGGGTCTCTC GGGGGCGAGG GCGAGGTTCA GGCCTTTCAG     360
GCCGCAGGAA GAGGAACGGA GCGAGTCCCC GCGCGCGGCG CGATTCCCTG AGCTGTGGGA     420
CGTGCACCCA GGACTCGGCT CACACATGCA GTTCGCTTTC CTGTTGGTGG GGGAACGCC      480
GATCGTGCGC ATCCGTCACC CCTCGCCGGC AGTGGGGGCT TGTGAACCCC CAAACCTG      538
```

(2) INFORMATION FOR SEQ ID NO:10:

(i) SEQUENCE CHARACTERISTICS:
        (A) LENGTH: 14 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 5..13
        (D) OTHER INFORMATION: /note= "Xaa represents isoleucine
            or leucine"

(xi) SEQUENCE DESCRIPTION: SEQ ID NO:10:

```
 Glu Ala Ala Thr Xaa Asp Xaa Pro Gln Gln Gly Ala Asn Lys
  1               5                   10
```

(2) INFORMATION FOR SEQ ID NO:11:

(i) SEQUENCE CHARACTERISTICS:
        (A) LENGTH: 534 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:11:

```
GGGTTGCGGA GGGTGGGCCT GGGAGGGGTG GTGGCCATTT TTTGTCTAAC CCTAACTGAG      60
AAGGGCGTAG GCGCCGTGCT TTGCTCCCC GCGCGCTGTT TTTCTCGCTG ACTTTCAGCG      120
GCGGAAAAG CCTCGGCCTG CCGCCTTCCA CCGTTCATTC TAGAGCAAAC AAAAAATGTC      180
AGCTGCTGGC CCGTTCGCCT CCCGGGGACC TGCGGCGGGT CGCCTGCCCA GCCCCCGAAC     240
CCCGCCTGGA GCCGCGGTCG GCCCGGGGCT TCTCCGGAGG CACCCACTGC CACCGCGAAG     300
AGTTGGGCTC TGTCAGCCGC GGGTCTCTCG GGGGCGAGGG CGAGGTTCAC GTTTCAGGC     360
CGCAGGAAGA GGAACGGAGC GAGTCCCGCC GCGGCGCGAT TCCCTGAGCT GTGGGACGTG     420
CACCCAGGAC TCGGCTCACA CATGCAGTTC GCTTTCCTGT TGGTGGGGGG AACGCCGATC     480
GTGCGCATCC GTCACCCCTC GCCGGCAGTG GGGCTTGTG AACCCCCAAA CCTG           534
```

HUMAN TELOMERASE

This is a divisional application of U.S. Ser. No. 08/676,974, filed on Jul. 8, 1996, now U.S. Pat. No. 5,770,422, which is incorporated herein by reference.

FIELD OF THE INVENTION

The field of this invention is an enzyme involved in cell replication.

BACKGROUND

DNA at chromosome ends is maintained in a dynamic balance of loss and addition of telomeric simple sequence repeats. Sequence loss occurs during cell replication, in part from incomplete replication of chromosome termini by DNA-dependent DNA polymerase. Telomeric repeat addition is catalyzed by the enzyme telomerase: a ribonucleoprotein enzyme which uses a short region within the RNA as a template for the polymerase reaction. Although cells can maintain a constant number of telomeric repeats by balancing repeat loss and addition, not all cells do so. Human germline and cancer cells maintain a constant number of telomeric repeats, while normal human somatic cells lose telomeric repeats with each cycle of cell division. Cells which do not maintain stable telomere length demonstrate a limited proliferative capacity: these cells senesce after a number of population doublings correlated with the erosion of telomeres to a critical minimum length.

Because normal somatic cells do not appear to express or require telomerase and do not maintain chromosome ends, and because all or almost all cancer cells express high levels of telomerase activity and maintain chromosome ends, molecules that inhibit or alter telomerase activity could provide effective and non-toxic anti-cancer agents. Similarly, inhibition of telomerase in parasitic or infectious agents (e.g. trypanosomes, fungi, etc.) could provide a specific approach for reducing the viability or proliferation of these agents. Conversely, activation of telomerase in proliferation-restricted cells (such as normal somatic cells of the blood, vasculature, liver, skin, etc.) could provide a mechanism for promoting additional proliferative lifespan.

RELEVANT LITERATURE

Purification of telomerase from the ciliate Tetrahymena and cloning of genes encoding two protein components of the enzyme is reported in Collins et al. (1995) Cell 81, 677–686 and copending U.S. Pat. application No. 08/359,125, filed Dec. 19, 1994. Literature relating to human telomerase include; Kim et al. (1994) Science 266, 2011–2014; and Feng et al. (1995) Science 269, 1236–1241. Literature relating to telomerase template modifications include Autexier et al. (1994) Genes and Devel 8, 563–575; Yu et al. (1991) Cell 67, 823–832; and Yu et al. (1990) Nature 344, 126–132. The Washington University-Merck EST Project contains an EST, reportedly deposited by Hillier et al. on Nov. 1, 1995, which has sequence similarity with the 3' end of SEQ ID NO:3, disclosed herein. For a general review, see Blackburn et al., Eds. (1995) Telomeres, Cold Spring Harbor Laboratory Press.

SUMMARY OF THE INVENTION

The invention provides methods and compositions relating to a human telomerase and related nucleic acids. Included are four distinct human telomerase subunit proteins, called p140, p105, p48 and p43 and telomerase protein domains thereof having telomerase-specific activity. The proteins may be produced recombinantly from transformed host cells from the subject telomerase encoding nucleic acids or purified from human cells. Also included are human telomerase RNA components, as well as specific, functional derivatives thereof.

The invention provides isolated telomerase hybridization probes and primers capable of specifically hybridizing with the disclosed telomerase gene, telomerase-specific binding agents such as specific antibodies, and methods of making and using the subject compositions in diagnosis (e.g. genetic hybridization screens for telomerase transcripts), therapy (e.g. gene therapy to modulate telomerase gene expression) and in the biopharmaceutical industry (e.g. reagents for screening chemical libraries for lead pharmacological agents and nucleic acid polymerase reagents).

SEQ ID LISTING

SEQ ID NO: 1: p105 protein (amino acid sequence)

SEQ ID NO: 2: p105 ambiguity maximized synthetic DNA

SEQ ID NO: 3: p105 natural cDNA (the coding region is bp 97–2370)

SEQ ID NO: 4: p105 E. coli optimized synthetic DNA

SEQ ID NO: 5: p105 mammalian optimized synthetic DNA

SEQ ID NO: 6: telomerase RNA

SEQ ID NO: 7: telomerase RNA template region modification 1

SEQ ID NO: 8: telomerase RNA template region modification 2

SEQ ID NO: 9: telomerase RNA template region modification 3

SEQ ID NO: 10 p43 peptide (XXXEAAT[I/L]D[I/L]PQQGANK, where the three X's are indeterminant residues)

DETAILED DESCRIPTION OF THE INVENTION

The invention provides isolated human telomerase proteins including human telomerase proteins p140, p105, p48 and p43, having molecular weights of about 140 kD, about 105 kD, about 48 kD and about 43 kD, respectively, as determined by polyacrylamide gel electrophoresis under denaturing conditions (Matsudaira and Burgess (1978) Anal Biochem 87, 386–396), and telomerase protein domains thereof. The telomerase proteins comprise assay-discernable functional domains including RNA recognition motifs and subunit binding domains and may be provided as fusion products, e.g with non-telomerase polypeptides. The human telomerase proteins of the invention, including the subject protein domains, all have telomerase-specific activity or function.

Telomerase-specific activity or function may be determined by convenient in vitro, cell-based, or in vivo assays: e.g. in vitro binding assays, cell culture assays, in animals (e.g. immune response, gene therapy, transgenics, etc.), etc. Binding assays encompass any assay where the molecular interaction of a telomerase protein with a binding target is evaluated. The binding target may be a natural intracellular binding target such as a telomerase subunit (e.g. another protein subunit or RNA subunit), a substrate, agonist, antagonist, chaperone, or other regulator that directly modulates telomerase activity or its localization; or non-natural binding target such a specific immune protein such as an antibody, or a telomerase specific agent such as those identified in assays described below. Generally, telomerase-binding specificity is assayed by telomere polymerase activity (see, e.g. Collins et al. 1995, Cell 81, 677–686), by binding equilibrium constants (usually at least about $10^7$ $M^{-1}$, preferably at least about $10^8$ $M^{-1}$, more preferably at least about $10^9$ $M^{-1}$), by the ability of the subject protein to function as negative mutants in telomerase-expressing cells, to elicit telomerase specific antibody in a heterologous host (e.g a rodent or rabbit), etc. In any event, the telomerase binding specificity of the subject telomerase proteins necessarily distinguishes ciliate telomerase, preferably distinguishes non-mammalian telomerases and more preferably distinguishes non-human telomerases. Exemplary telomerase proteins which are shown to have telomerase binding specificity include the telomerase RNA (e.g. SEQ ID NO:6) binding domains (e.g. RRM 1–4: SEQ ID NO:1, about residues 5–81, residues 115–192, residues 336–420, and residues 487–578, respectively), telomerase primer binding domains, nucleotide triphosphate binding domains and binding domains of regulators of telomerase such as nuclear localization proteins, etc. As used herein, a protein domain comprises at least 12, preferably at least about 20, more preferably at least about 40, most preferably at least about 80 residues of the disclosed respective SEQ ID NO.

The claimed human telomerase proteins are isolated or pure: an "isolated" protein is unaccompanied by at least some of the material with which it is associated in its natural state, preferably constituting at least about 0.5%, and more preferably at least about 5% by weight of the total protein in a given sample and a pure protein constitutes at least about 90%, and preferably at least about 99% by weight of the total protein in a given sample. The telomerase proteins and protein domains may be synthesized, produced by recombinant technology, or purified from human cells. A wide variety of molecular and biochemical methods are available for biochemical synthesis, molecular expression and purification of the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, New York) or that are otherwise known in the art. An exemplary method for isolating each of human telomerase protein p140, p105, p48 and p43 from human cells is as follows:

Several thousand (two to twelve thousand) liters of HeLa cells are grown in spinner culture. The cells are lysed by dounce homogenization in low-salt buffer to produce crude cell lysates. The lysates are supplemented with 15% glycerol and centrifuged at 125,000×g for 50 minutes to obtain a first soluble fraction enriched for telomerase activity (S-100 fraction). The S-100 fraction is adjusted to 0.2 M ammonium sulfate, bound to SP Sepharose (Pharmacia), and developed with a gradient in sodium chloride, to obtain a second soluble fraction enriched for telomerase (SP fraction). The SP fraction is adjusted to about 0.3–0.4 M ionic strength and bound to Q Sepharose (Pharmacia), and developed with a gradient in sodium chloride, to obtain a third soluble fraction enriched for telomerase (Q fraction). The Q fraction is adjusted to about 0.3–0.4 M ionic strength, bound to phosphocellulose (Whatman), and developed with sodium chloride, to obtain a fourth soluble fraction enriched for telomerase (PC fraction). The PC fraction is adjusted to about 0.3–0.4 M ionic strength, bound to 2'Omethyl RNA oligonucleotide immobilized on streptavidin agarose (Sigma), and eluted with a electrophoresis sample medium comprising 5% β-mercaptoethanol and 2% Sodium Dodecyl Sulfate to obtain a fifth soluble fraction (2'Omethyl fraction). The 2'Omethyl fraction is separated by polyacrylamide gel electrophoresis under denaturing conditions (Matsudaira and Burgess (1978) Anal Biochem 87, 386–396) to obtain gel protein bands at a molecular weight of about 140 kD, 105 kD, 48 kD or 43 kD having telomerase activity. The gel bands are excised or blotted to obtain purified human telomerase proteins p140, p105, p48 and p43.

The subject telomerase proteins find a wide variety of uses including use in isolating, enriching for and concentrating telomerase RNA and telomerase proteins, as immunogens, in the methods and applications described below, as reagents in the biotechnology industries, and in therapy. Recombinant telomerases are used in many applications where nascent oligonucleotides of predetermined sequence are desired. For example, native nucleic acid molecules are labeled or extended at their 3' ends by addition of a precleterrnined repeat sequence (for double-stranded oligonucleotides, both ends of the molecule may be tagged). Oligonucleotides complementary to the repeat are then used to amplify, sequence, affinity purify, etc. the nucleic acid molecules. The use of a repeat sequence for 3' end tagging improves specificity and provides sequence alternatives compared with non-templated enzymes presently available for this purpose, e.g. terminal transferase. Repeats encoding restriction enzyme sites provide repeat tagging to facilitate cloning and the use of telomerase alleviates the restrictive conditions required for optimal ligation with available ligase enzymes. Telomerase also finds use in regulating cell growth or increasing cell density tolerance; for example, cells contacted with an effective amount of exogenous telomerase to overcome the growth control limitation otherwise imposed by short telomere length. Telomerase may be introduced, expressed, or repressed in specific populations of cells by any convenient way such as microinjection, promoter-specific expression of recombinant enzyme, targeted delivery of lipid vesicles, etc. Advantageously, only a brief period of telomerase activity is required to allow many generations of continued proliferation of the contacted cell, due to the ability of telomerase to extend telomeres in one cell cycle by more sequence than is lost with each cell division.

The invention provides natural and non-natural human telomerase-specific binding agents including substrates, agonist, antagonist, etc., methods of identifying and making such agents, and their use in diagnosis, therapy and pharmaceutical development. For example, human telomerase-specific agents are useful in a variety of diagnostic and therapeutic applications. Novel human telomerase-specific binding agents include human telomerase-specific receptors, such as somatically recombined protein receptors like specific antibodies or T-cell antigen receptors (see, e.g Harlow and Lane (1988) Antibodies, A Laboratory Manual, Cold Spring Harbor Laboratory) and other natural intracellular binding agents identified with assays such as one-, two- and three-hybrid screens, non-natural intracellular binding agents identified in screens of chemical libraries such as described below, etc. Agents of particular interest modulate human telomerase function, e.g. human telomerase antgonists and find use methods for modulating the binding of a human telomerase or telomerase protein to a human telomerase binding target.

For diagostic uses, the binding agents are frequently labeled, such as with fluorescent, radioactive, chemiluminescent, brother easily detectable molecules, either conjugated directly to the binding agent or conjugated to a probe specific for the binding agent. Binding agents also find use in modulating the telomerase activity present in a cell. For example, isolated cells, whole tissues, or individuals may be treated with a telomerase binding agent to activate, inhibit, or alter the specificity of telomerase assembly, localization, substrate interaction, or synthesis activity. Effectively treated cells have increased or decreased replication potential, or suffer from loss of proper telomere structure (resulting in lethality). These binding agents also find therapeutic use to control cell proliferation; for example, the uncontrolled growth of transformed cells (e.g. cancer cells) is managed by administration to the cells or patient comprising such cells of a telomerase binding agent which reduces telomerase activity. In contrast to many current chemotherapies, the present invention provides enhanced specificity of lethality, with minimum toxicity to dividing yet normal somatic cells.

The amino acid sequences of the disclosed telomerase proteins are used to back-translate telomerase protein-encoding nucleic acids optimized for selected expression systems (Holler et al. (1993) Gene 136, 323–328; Martin et al. (1995) Gene 154, 150–166) or used to generate degenerate oligonucleotide primers and probes for use in the isolation of natural telomerase encoding nucleic acid sequences ("GCG" software, Genetics Computer Group, Inc, Madison Wis.). As examples, SEQ ID NO:2 discloses an ambiguity-maximized p105 coding sequence encompassing all possible nucleic acids encoding the full-length p105 protein. SEQ ID NO:3 discloses a natural human cDNA sequence encoding p105, SEQ ID NO:4 is a p105 coding sequence codon-optimized for *E. coli*, SEQ ID NO:5 is a p105 coding sequence codon optimized for mammalian cell expression. Telomerase encoding nucleic acids may be part of human telomerase-expression vectors and may be incorporated into recombinant host cells, e.g. for expression and screening, transgenic animals, e.g. for functional studies such as the efficacy of candidate drugs for disease associated with human telomerase-mediated signal transduction, etc. Expression systems are selected and/or tailored to effect human telomerase protein structural and functional variants through alternative post-translational processing.

The invention also provides nucleic acid hybridization probes and replication/amplification primers having a human telomerase cDNA specific sequence contained in SEQ ID NO:3, bases 1–2345, and sufficient to effect specific hybridization thereto (i.e. specifically hybridize with SEQ ID NO:3, bases 1–2345 in the presence of natural ciliate telomerase cDNA, preferably in the presence of non-mammalian telomerase cDNA and more preferably, in the presence of murine telomerase cDNA). Demonstrating specific hybridization generally requires stringent conditions, for example, hybridizing in a buffer comprising 30% formamide in 5×SSPE (0.18 M NaCl, 0.01 M NaPO$_4$, pH7.7, 0.001 M EDTA) buffer at a temperature of 42° C. and remaining bound when subject to washing at 42° C. with 0.2×SSPE; preferably hybridizing in a buffer comprising 50% formamide in 5×SSPE buffer at a temperature of 42° C. and remaining bound when subject to washing at 42° C. with 0.2×SSPE buffer at 42° C. Human telomerase cDNA homologs can also be distinguished from other protein using alignment algorithms, such as BLASTX (Altschul et al (1990) Basic Local Alignment Search Tool, J Mol Biol 215, 403–410).

The invention also provides non-natural sequence, recombinant and isolated natural sequence human telomerase RNA. Natural human telomerase RNA sequences include the nucleic acid disclosed as SEQ ID NO:6, or a fragment thereof sufficient to specifically hybridize with a nucleic acid having the sequence defined by SEQ ID NO:6 in the presence of a nucleic acid having the sequence disclosed in Feng et al. 1995, Science 269, 1236–1241 (SEQ ID NO.11). Such fragments necessarily distinguish the previously described (Feng et al. 1995, Science 269, 1236–1241) human RNA species. Preferred such fragments comprise SEQ ID NO:6, bases 191–210, bases 245–259, bases 341–369 or bases 381–399. Non-natural sequences include derivatives and/or mutations of SEQ ID NO:6, where such derivatives/mutations provide alteration in template, protein binding, or other regions to effect altered telomerase substrate specificity or altered reaction product (e.g. any predetermined sequence), etc.; see, e.g. Autexier et al., 1994, Genes & Develop 8, 563–575; Collins et al. (1995) EMBO J. 14, 5422–5432; Greider et al. (1995) Structure and Biochemistry of Ciliate and Mammalian Telomerases, in DNA Replication, DePamphlis, Ed., Cold Spring Harbor Laboratory Press. Additional derivatives function as dominant negative fragments which effectively compete for telomerase assembly. For examples, SEQ ID NO:7, 8 and 9 are derivatives which provide for modified substrate specificity and polymerase reaction product to interfere with cellular function (see, e.g. Hanish et al. (1994) Proc Natl Acad Sci 91, 8861–8865).

The subject nucleic acids are of synthetic/non-natural sequences and/or are isolated, i.e. unaccompanied by at least some of the material with which it is associated in its natural state, preferably constituting at least about 0.5%, preferably at least about 5% by weight of total nucleic acid present in a given fraction, and usually recombinant, meaning they comprise a non-natural sequence or a natural sequence joined to nucleotide(s) other than that which it is joined to on a natural chromosome. Nucleic acids comprising the nucleotide sequence of SEQ ID NO:3 or fragments thereof, contain such sequence or fragment at a terminus, immediately flanked by a sequence other than that which it is joined to on a natural chromosome, or flanked by a native flanking region fewer than 10 kb, preferably fewer than 2 kb, which is immediately flanked by a sequence other than that which it is joined to on a natural chromosome. While the nucleic acids are usually RNA or DNA, it is often advantageous to use nucleic acids comprising other bases or nucleotide analogs to provide modified stability, etc. The subject nucleic acids find a wide variety of applications including use as translatable transcripts, hybridization probes, PCR primers, diagnostic nucleic acids, etc.; use in detecting the presence of human telomerase genes and gene transcripts and in detecting or amplifying nucleic acids encoding additional human telomerase homologs and structural analogs.

In diagnosis, human telomerase hybridization probes find use in identifying wild-type and mutant human telomerase alleles in clinical and laboratory samples. Mutant alleles are used to generate allele-specific oligonucleotide (ASO) probes for high-throughput clinical diagnoses. In therapy, therapeutic human telomerase nucleic acids are used to modulate cellular expression or intracellular concentration or availability of active telomerase. A wide variety of indications may be treated, either prophylactically or therapeutically with the subject compositions. For example, where limitation of cell growth is desired, e.g. neoproliferative disease, a reduction in telomerase expression is effected by introducing into the targeted cell type human telomerase nucleic acids which reduce the functional expression of human telomerase gene products (e.g. nucleic acids capable of inhibiting translation of a functional telomerase transcript). Conditions for treatment include various cancers, where any of a wide variety of cell types may be involved, restenosis, where vascular smooth muscle cells are involved, inflammatory disease states, where endothelial cells, inflammatory cells and glomerular cells are involved, myocardial infarction, where heart muscle cells are involved, glomerular nephritis, where kidney cells are involved, transplant rejection where endothelial cells are involved, infectious diseases such as HIV infection where certain immune cells and other infected cells are involved, or the like.

Telomerase inhibitory nucleic acids are typically antisense: single-stranded sequences comprising complements of the disclosed natural telomerase coding sequences. Antisense modulation of the expression of a given telomerase protein may employ telomerase antisense nucleic acids operably linked to gene regulatory sequences. Cell are transfected with a vector comprising a human telomerase sequence with a promoter sequence oriented such that transcription of the gene yields an antisense transcript capable of binding to endogenous human telomerase protein encoding mRNA. Transcription of the antisense nucleic acid may be constitutive or inducible and the vector may provide for stable extrachromosomal maintenance or integration. Alternatively, single-stranded antisense nucleic acids that bind to genomic DNA or mRNA encoding a given human telomerase protein may be administered to the target cell, in or temporarily isolated from a host, at a concentration that results in a substantial reduction in expression of the targeted protein.

In other indications, e.g. certain hypersensitivities, atrophic diseases, etc., an increase in cell growth or proliferation is desired. In these applications, an enhancement in human telomerase expression is effected by introducing into the targeted cell type human telomerase nucleic acids which increase the functional expression of human telomerase gene products. Conditions for treatment include multiple sclerosis, where certain neuronal cells are involved, inflammatory disease states such as rheumatoid arthritis, where bystander cells are involved, transplant rejection where graft cells are involved, infectious diseases such as HIV infection where certain uninfected host cells are involved, or the like. Such nucleic acids may be human telomerase expression vectors, vectors which upregulate the functional expression of an endogenous human telomerase allele, or replacement vectors for targeted correction of human telomerase mutant alleles.

Various techniques may be employed for introducing of the nucleic acids into viable cells, e.g. transfection with a retrovirus, viral coat protein-liposome mediated transfection. The techniques vary depending upon whether one is using the subject compositions in culture or in vivo in a host. In some situations it is desirable to provide the nucleic acid source with an agent which targets the target cells, such as an antibody specific for a surface membrane protein on the target cell, a ligand for a receptor on the target cell, etc. Where liposomes are employed, proteins which bind to a surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life.

The invention provides methods and compositions for enhancing the yield of many recombinantly produced proteins by increasing maximum cell densities and survival time of host production cells in culture. Specifically, cultured cells are transfected with nucleic acids which effect the up-regulation of endogenous telomerase or the expression of an exogenous telomerase. For example, nucleic acids encoding functional human telomerase operably linked to a transcriptional promoter are used to over-express the exogenous telomerase in the host cell. Telomerase-expressing cells demonstrate enhanced survival ability at elevated cell densities and over extended culture periods.

The invention provides efficient methods of identifying agents, compounds or lead compounds for agents active at the level of a human telomerase modulatable cellular function. Generally, these screening methods involve assaying for compounds which modulate human telomerase interaction with a natural human telomerase binding target. A wide variety of assays for binding agents are provided including labeled in vitro telomere polymerase assays, proteinprotein binding assays, immunoassays, cell based assays, etc. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development. Target indications may include infection, genetic disease, cell growth and regulatory disfunction, such as neoplasia, inflammation, hypersensitivity, etc. Target cells also include progenitor cells for repopulating blood or bone marrow, tissue grafts, and tissue subject to degredation/high turnover such as digestive and vascular endothelia and pulmunary and dermal epithelia.

In vitro binding assays employ a mixture of components including a human telomerase protein, which may be part of multi-subunit telomerase, a fusion product with another peptide or polypeptide, e.g. a tag for detection or anchoring, etc. The assay mixtures comprise a natural intracellular human telomerase binding target, e.g. a substrate. While native binding targets may be used, it is frequently preferred to use portions (e.g. peptides, nucleic acid fragments) thereof so long as the portion provides binding affinity and avidity to the subject human telomerase conveniently measurable in the assay. The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like salts, buffers, neutral proteins, e.g. albumin, detergents, protease inhibitors, nuclease inhibitors, antimicrobial agents, etc. may be used.

The resultant mixture is incubated under conditions whereby, but for the presence of the candidate pharmacological agent, the human telomerase specifically binds the cellular binding target, portion or analog with a reference binding affinity. The mixture components can be added in any order that provides for the requisite bindings and incubations may be performed at any temperature which facilitates optimal binding. Incubation periods are likewise selected for optimal binding but also minimized to facilitate rapid, high-throughput screening.

After incubation, the agent-biased binding between the human telomerase and one or more binding targets is detected by any convenient way. For cell-free binding type assays, a separation step is often used to separate bound from unbound components. Separation may be effected by precipitation (e.g. TCA precipitation, immunoprecipitation, etc.), immobilization (e.g on a solid substrate), etc., followed by washing by, for examples, membrane filtration (e.g. Whatman's P-81 ion exchange paper, Polyfiltronic's hydrophobic GFC membrane, etc.), gel chromatography (e.g. gel filtration, affinity, etc.). For telomere polymerase assays, binding is detected by a change in the polymerization by the telomerase of a nucleic acid or nucleic acid analog on the substrate.

Detection may be effected in any convenient way. For cell-free binding assays, one of the components usually comprises or is coupled to a label. The label may provide for direct detection as radioactivity, luminescence, optical or electron density, etc. or indirect detection such as an epitope tag, an enzyme, etc. A variety of methods may be used to detect the label depending on the nature of the label and other assay components, e.g. through optical or electron density, radiative emissions, nonradiative energy transfers, etc. or indirectly detected with antibody conjugates, etc.

A difference in the binding affinity of the human telomerase protein to the target in the absence of the agent as compared with the binding affinity in the presence of the agent indicates that the agent modulates the binding of the human telomerase protein to the human telomerase binding target. Analogously, in the cell-based transcription assay also described below, a difference in the human telomerase transcriptional induction in the presence and absence of an agent indicates the agent modulates human telomerase-induced transcription. A difference, as used herein, is statistically significant and preferably represents at least a 50%, more preferably at least a 90% difference.

The following examples are offered by way of illustration and not by way of limitation.

EXAMPLES

1. Protocol for high-throughput human telomere polymerization assay.

A. Reagents:
Neutralite Avidin: 20 μg/ml in PBS.
human telomerase: $10^{-8}$–$10^{-5}$M human telomerase in PBS.
Blocking buffer: 5% BSA, 0.5% Tween 20 in PBS; 1 hour at room temperature.
Assay Buffer: 100 mM KCl, 20 mM HEPES pH 7.6, 1 mM MgCl$_2$, 1 mM dATP, 1 mM dTTP, 1% glycerol, 0.5% NP-40, 50 mM BME, 1 mg/ml BSA, cocktail of protease inhibitors.
[$^{32}$P]α-dGTP 10×stock: 2×10$^{-5}$ M "cold" dGTP with 100 μCi [$^{32}$P]α-dGTP. Place in the 4° C. microfridge during screening.
telomerase substrate: $10^{-7}$–$10^{-4}$M biotinylated telomerase substrate (5'-biotin-d(TTAGGG)$_3$-3'] in PBS.
Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml of PBS.

B. Preparation of assay plates:
Coat with 120 μl of stock N Avidin per well overnight at 4° C.
Wash 2 times with 200 μl PBS.
Block with 150 μl of blocking buffer.
Wash 2 times with 200 μl PBS.

C. Assay:
Add 40 μl assay buffer/well.
Add 40 μl human telomerase (1–1000 fmoles/40 μl in assay buffer)
Add 10 μl compound or extract.
Add 10 μl [$^{32}$P]α-dGTP 10× stock.
Add 40 μl biotinylated telomerase substrate (0.1–10 pmoles/40 ul in assay buffer)
Shake at 25° C. for 15 minutes.
Incubate additional 45 minutes at 25° C.
Stop the reaction by washing 4 times with 200 μl PBS.
Add 150 μl scintillation cocktail.
Count in Topcount.

D. Controls for all assays (located on each plate):
a. Non-specific binding
b. cold dGTP at 80% inhibition.

2. Protocol for high throughput human telomerase subunit-RNA complex formation assay.

A. Reagents:
Neutralite Avidin: 20 μg/ml in PBS.
Blocking buffer: 5% BSA, 0.5% Tween 20 in PBS; 1 hour at room temperature.
Assay Buffer: 100 mM KCl, 20 mM HEPES pH 7.6, 1 mM MgCl$_2$, 1 % glycerol, 0.5% NP-40, 50 mM β-mercaptoethanol, 1 mg/ml BSA, cocktail of protease inhibitors.
$^{33}$P human telomerase protein 10×stock: $10^{-8}$–$10^{-6}$M "cold" human telomerase subunit (p105) supplemented with 200,000–250,000 cpm of labeled human telomerase (Beckman counter). Place in the 4° C. microfridge during screening.
Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml of PBS.
telomerase RNA: $10^{-7}$–$10^{-4}$M biotinylated RNA (SEQ ID NO:6) in PBS.

B. Preparation of assay plates:
Coat with 120 μl of stock N-Avidin per well overnight at 4° C.
Wash 2 times with 200 μl PBS.
Block with 150 μl of blocking buffer.
Wash 2 times with 200 μl PBS.

C. Assay:
Add 40 μl assay buffer/well.
Add 10 μl compound or extract.
Add 10 μl $^{33}$P-human telomerase protein (20,000–25,000 cpm/0.1–10 pmoles/well=$10^{-9}$–$10^{-7}$M final concentration).
Shake at 25° C. for 15 minutes.
Incubate additional 45 minutes at 25° C.
Add 40 μl biotinylated RNA (0.1–10 pmoles/40 μl in assay buffer)
Incubate 1 hour at room temperature.
Stop the reaction by washing 4 times with 200 μl PBS.
Add 150 μl scintillation cocktail.
Count in Topcount.

D. Controls for all assays (located on each plate):
a. Non-specific binding
b. Soluble (non-biotinylated telomerase) at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated telomerase nucleic acid comprising at least one of nucleotides 191–210, nucleotides 245–259, nucleotides 341–369 and nucleotides 381–399 of SEQ ID NO:6.

2. An isolated telomerase nucleic acid according to claim 1 comprising SEQ ID NO:6.

3. An isolated human telomerase nucleic acid comprising a derivative or mutation of SEQ ID NO:6 which provides altered substrate specificity or altered reaction product, wherein the derivative or mutation comprises a nucleotide sequence selected from the group consisting of SEQ ID NO:7, SEQ ID NO:8 or SEQ ID NO:9.

4. An isolated human telomerase nucleic acid according to claim 3, wherein the derivative or mutation comprises SEQ ID NO:7.

5. An isolated human telomerase nucleic acid according to claim 3, wherein the derivative or mutation comprises SEQ ID NO:8.

6. An isolated human telomerase nucleic acid according to claim 3, wherein the derivative or mutation comprises SEQ ID NO:9.

* * * * *